United States Patent [19]

Dörschug et al.

[11] Patent Number: 5,101,013
[45] Date of Patent: Mar. 31, 1992

[54] PROCESS FOR ISOLATING BASIC PROTEINS FROM PROTEIN MIXTURES

[75] Inventors: Michael Dörschug, Bochum; Ranier Obermeier, Hattersheim am Main, both of Fed. Rep. of Germany

[73] Assignee: Hoechst Aktiengesellschaft, Frankfurt am Main, Fed. Rep. of Germany

[21] Appl. No.: 230,085

[22] Filed: Aug. 9, 1988

[30] Foreign Application Priority Data

Aug. 11, 1987 [DE] Fed. Rep. of Germany ....... 3726655

[51] Int. Cl.$^5$ .......................... C07K 5/00; C07K 3/22
[52] U.S. Cl. ................................... 530/305; 530/303; 530/412; 530/416; 530/417
[58] Field of Search ............... 530/303, 305, 412, 417, 530/416

[56] References Cited

U.S. PATENT DOCUMENTS 4,129,560 12/1978 Zoltobrocki ........................ 530/305
4,644,057 2/1987 Bicker et al. ........................ 530/309

FOREIGN PATENT DOCUMENTS

31724/77 6/1979 Australia .
0000439 1/1979 European Pat. Off. .
0087932 9/1983 European Pat. Off. .
0123228A 10/1984 European Pat. Off. .
2173503 10/1986 United Kingdom .

OTHER PUBLICATIONS

Wilson, Chem. Abst., 104, 84(1986) Entry No. 62218b.
D. Steiner et al., J. Biol. Chem., vol. 246, No. 5, pp. 1365-1374, (1971).
J. Markussen et al., Protein Engineering, vol. 1, No. 3, pp. 205-213 (1987).
U. Krabieli et al., Chemical Abstracts, vol. 108, No. 226915 (1988).

Primary Examiner—F. T. Moezie
Attorney, Agent, or Firm—Finnegan, Henderson, Farabow, Garrett and Dunner

[57] ABSTRACT

Basic proteins are isolated from protein mixtures which contain such basic proteins and which are obtained by enzymatic clevage of proinsulin and/or its derivatives of natural, semisynthetic or genetic engineering origin by ion exchanger chromatography on strongly acid cation exchangers.

13 Claims, 1 Drawing Sheet

PROCESS FOR ISOLATING BASIC PROTEINS FROM PROTEIN MIXTURES

BACKGROUND OF THE INVENTION

In the preparation of human insulin by genetic engineering methods, biosynthesis of the insulin is carried out via a precursor molecule called proinsulin. In this, the B chain is linked to the A chain by the C peptide (=connecting peptide). In genetic engineering production by means of *Escherichia coli*, a fusion protein in which another foreign protein, for example β-galactosidase, precedes the proinsulin is sometimes first obtained. This foreign protein must first be split off, for example by treatment with a cyanogen halide, before further working up (compare German Offenlegungsschrift 34 40 988). After the cyanogen halide cleavage, cysteine radicals are converted into their S-sulfonate form by sulfitolysis (treatment with sodium sulfite and sodium tetrathionate). The molecule can be converted from this form into its natural spatial structure with correct formation of its disulfide bridges by reductive folding back (for example by treatment with mercaptoethanol in basic solution). The proinsulin or preproinsulin (=derivative of proinsulin; the prefix "pre" relates to one or more additional amino acids on the N terminus of the proinsulin) is converted by enzymatic cleavage (for example with trypsin) into a cleavage mixture which contains an insulin precursor, insulin-Arg-B31-B32, and the C peptide. In addition to these, some by-products, such as, for example, insulin-Des-Thr-B30, insulin-Arg-B31 and incompletely cleaved intermediates, are also formed.

The insulin derivatives mentioned and compounds which are formed in preliminary stages by chemical treatment of the starting material must be separated from one another.

It is particularly difficult here to separate insulin derivatives of basic character which have derivatizations on amino acids which, after formation of the tertiary structure, lie inside the molecule.

This is found in a comparison experiment (see Part B): the anion exchanger process which has been described in German Patent 26 29 568 and has been developed for purification of insulin has the peculiarity that a nonionic surfactant is added in order to avoid protein aggregations of the elution liquid. This process, which is particularly suitable for the purification of insulins, leads to a completely inadequate separation in the attempt to separate and isolate basic proteins which are obtained, for example, by tryptic cleavage of proinsulin of genetic engineering origin. This is illustrated by the corresponding elution profile (see Part B); it can be seen that the peaks for the individual peptides overlap one another.

Processes are also already known which are said to achieve separation of the proinsulin cleavage products mentioned. Steiner et al. describe in "Journ. of Biol. Chem.", 246, pages 1365–1374 (1971) a process for isolating C peptide from a proinsulin cleavage mixture. In this process (no yields are stated), chromatography is carried out over a weakly acid cellulose-based cation exchanger containing carboxymethyl groups (CM). 7 mol/l of urea are added here to the loading and elution solution in order to avoid aggregation of the proteins. The presence of such high urea concentrations is a disadvantage because it leads to derivatization of proteins, above all to carbamoylation of free amino groups.

Markussen et al. describe in "Protein Engineering" Volume 1 No. 3, pages 205–213 (1987) an anion exchanger chromatography process on diethyl-2-hydroxypropylaminoethyl-containing (QAE) anion exchangers on a matrix of a three-dimensional crosslinked polysaccharide network.

This process—no yields are given for the anion exchange chromatography—is carried out in 60% strength ethanol solution to inhibit protein aggregations. The safety measures required, which are particularly necessary when working with concentrated organic solvents on an industrial scale, are a disadvantage of ethanol solutions of such a concentration. On the other hand, as reworking has shown, denaturations of the proteins occur at the alcohol concentrations mentioned.

SUMMARY OF THE INVENTION

In the efforts to provide a better separation and isolation process for basic proteins from protein mixtures—containing such basic proteins—it has been found, surprisingly, that this aim can be achieved by chromatography of the protein mixtures on strongly acid cation exchangers and elution by means of aqueous alkanol with only a relatively small amount of alkanol. It is particularly surprising that it is possible both to improve the separation capacity in comparison with the prior art and largely to avoid the additional derivatizations of the proteins during the separation. Derivatives which contain derivatizations—formed during the pretreatment of the proinsulin—inside the proteins present in the tertiary structure can astonishingly even be separated off. No aggregations of the proteins to be separated are observed. Reusability of the exchangers presents no difficulties.

DETAILED DESCRIPTION OF THE INVENTION

Figure 1:
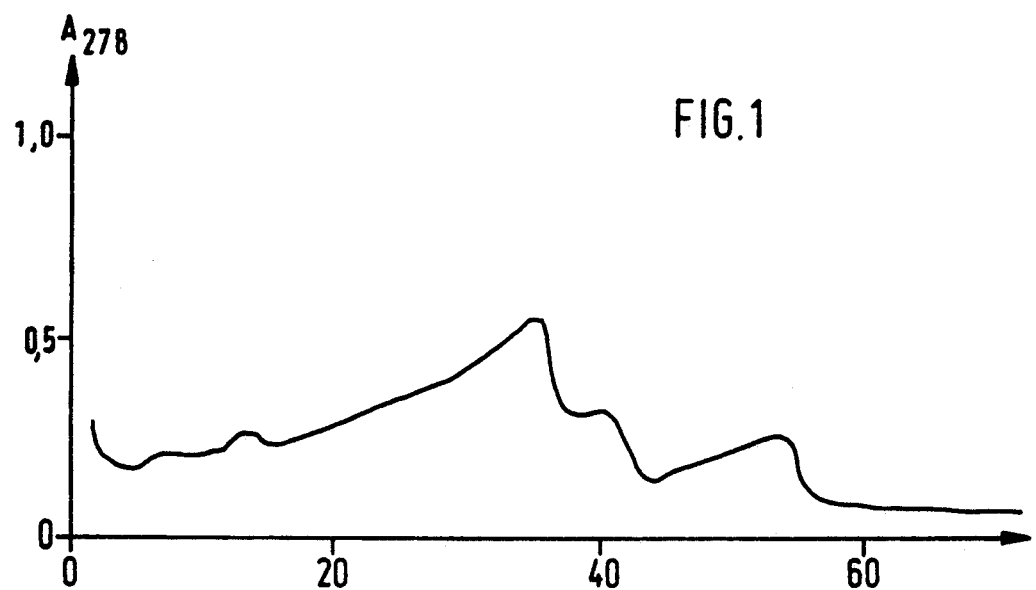
FIG. 1 shows the elution profile of comparison Example 1, recorded during the elution. The method of Example 1 employs an anion-exchange process with a nonionic surfactant for purification of proteins.

The invention accordingly relates to a process for the isolation of basic proteins from protein mixtures which contain such basic proteins and which have been obtained by enzymatic cleavage of proinsulin and/or its derivatives of natural, semisynthetic or genetic engineering origin by charging an ion exchanger with the protein mixture and elution, which comprises using a strongly acid cation exchanger as the ion exchanger and carrying out the elution by means of an $H_2O/C_1$–$C_4$-alkanol mixture which contains about 10 to 50% by volume, preferably about 20 to 40% by volume and in particular about 30% by volume, of alkanol. The basic proteins can be isolated in high yields from cleavage mixtures of any desired proinsulins or of derivatives thereof, such as, for example, monkey preproinsulin, by the process according to the invention. Possible ion exchangers are in principle all the strongly acid cation exchangers. Strongly acid cation exchangers in which the functional group is the sulfo group, in particular the sulfopropyl group —$CH_2$—$CH_2$—$CH_2$—$SO_3H$, for example on a matrix of hydrophilic vinyl polymers containing hydroxyl groups (for example (®)Fractogel TSK, manufacturer Merck, Darmstadt), acrylic copolymers (for example SP (®)Tris-acryl M, manufacturers Réactifs IBF, Villeneuve-la-Garenne, France) or gels with a content of crosslinked agarose (for example S-(®) Sepharose, manufacturer Pharmacia, Upsala, Sweden) are preferred; S-Sepharose is particularly preferred.

Before loading of the strongly acid cation exchanger with the cleavage mixture, this should be freshly equilibrated with a buffer solution. This buffer solution preferably consists of a water/$C_1$-$C_4$-alkanol mixture with an alkanol content of preferably about 10 to 50% by volume, particularly preferably about 20 to 40% by volume and in particular about 30% by volume. Preferred alkanols are ethanol and isopropanol, in particular isopropanol. Further additives which can be added to the buffer solution are, for example, salt, preferably physiologically tolerated mineral salt, one or more of any desired organic acids, preferably lactic acid, a base, preferably NaOH, and/or preservatives. The preferred pH of the buffer solution is between about 2.5 and 5.5, particularly preferably between about 3.5 and 4.0.

Loading of the strongly acid cation exchanger can be carried out by dissolving the cleavage mixture in a buffer solution—preferably with the composition described above and the pH described above—and bringing the resulting solution into contact with the strongly acid cation exchanger.

The elution solution, which in principle can have a composition similar to that of the buffer solution described above, preferably has a pH of 3.5 to 4.0. An elution process in which the elution solution has a concentration/time gradient of the salt with preferably a linear course is particularly suitable. This concentration gradient can be set up, for example, such that a low salt concentration (in the limit case towards 0) is present in the elution solution at the start of the elution and the salt concentration is increased during the elution process. Particularly effective separation of the protein mixture can be achieved in this manner. A preferred salt concentration gradient varies from almost 0 mole of salt/l (at the start of the elution) to about 1 mole of salt/l (at the end of the elution), particularly preferably from about 0.15 (at the start of the elution) to about 0.35 mole/l (at the end of the elution). Many organic and inorganic salts are possible for the salt addition. Physiologically tolerated salts, such as ammonium and alkali metal salts, are preferred, and sodium salts, in particular sodium chloride, are especially preferred.

The separation process according to the invention can be carried out in various ways. The procedure by a column process or a batch process is to be preferred.

The temperature, which is preferably to be kept constant during the ion exchanger chromatography, can be varied within a wide range. A temperature interval from about $-10°$ C. to about $50°$ C., in particular about $15°$ to about $25°$ C., is to be preferred.

The invention is illustrated in more detail by the following embodiment example (A). The superiority of the process according to the invention over a process for insulin purification according to the prior art (German Patent 26 29 568) will be demonstrated by the subsequent comparison (B).

A) Embodiment Example (according to the invention) 6 l of S-Sepharose are suspended in an aqueous buffer solution which contains 50 mmol/l of lactic acid, 30% of isopropanol and 1 mole/l of sodium chloride and has a pH of about 3.5, and a column with a diameter of 10 cm is filled with the suspension to a level of about 80 cm. The column is equilibrated with 10 l of aqueous starting buffer solution (50 mmol/l of lactic acid, 30% of isopropanol, 0.15 mol/l of sodium chloride, pH about 3.5). 15 g of crystallized cleavage mixture which contains 6.2 g of insulin-Arg-B31-32, 3 g of insulin-Arg-B31 and insulin-Des-Thr-B30 and unknown cleavage intermediates and derivatives and has been formed by tryptic cleavage of human preproinsulin are dissolved in 3 l of the starting buffer and the solution is applied to the column. The column is then eluted with an aqueous solution containing 50 mmol/l of lactic acid and 30% of isopropanol at a pH of 3.5 (adjusted with NaOH) and a gradient of 0.15 mol/l to 0.35 mol/l of sodium chloride. The elution solution has a volume of 2 x 20 l. The flow rate is 1.5 l/hour. Fractions with an insulin-Arg-B31-32 content of more than 90% according to HPLC (high pressure liquid chromatography) are collected, diluted with $H_2O$ in a ratio of 1:1 and precipitated by adding 10 ml of 10% strength $ZnCl_2$ solution/l of solution and bringing the pH to 6.8. The yield is 5 g of insulin-Arg-B31-32, which corresponds to a stage yield, based on insulin-Arg-B31-32, of 80%.

B) Comparison

Figure 2:
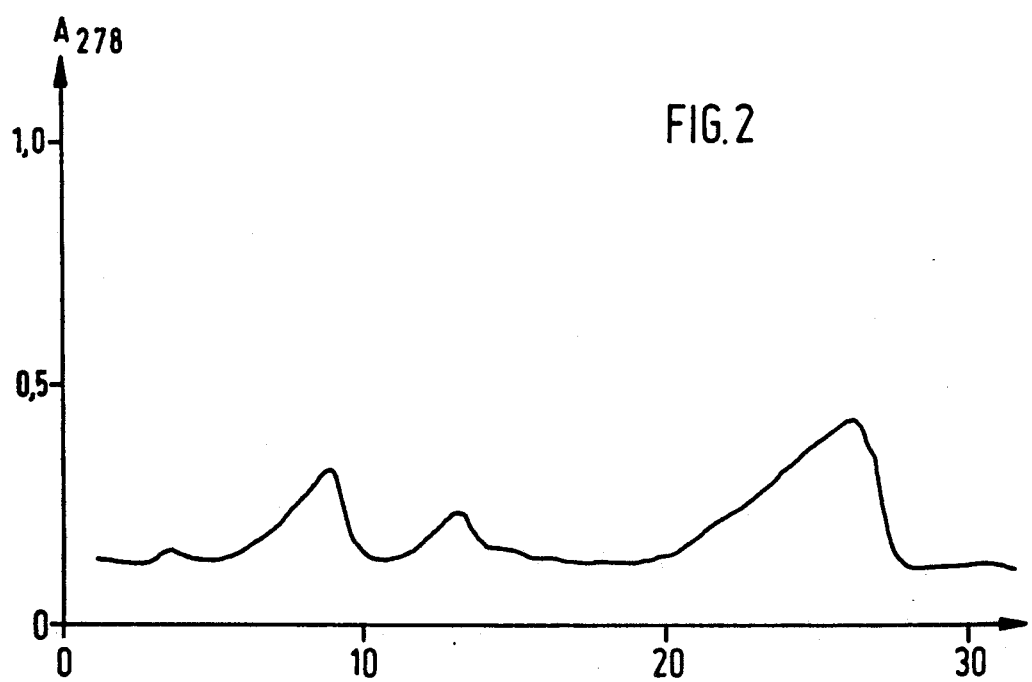
FIG. 2 shows the elution profile of Example 2 carried out according to the invention, recorded during the elution. The method of Example 2 employs chromatography of protein mixtures on a strongly acidic cation exchanger and elution by means of aqueous alkanol.

Comparison Example I was carried out according to German Patent 26 29 568 and Example II was carried out according to the invention. The process parameters and the results achieved are compared in Table 1. FIG. 1 shows the elution profile of Comparison Example I recorded during the elution and FIG. 2 shows that of Example II according to the invention. The absorption A in the UV range at a wavelength of 278 nm ($A_{278}$) is plotted against the elution time and the fraction numbers. The elution profiles show that the process according to the invention leads to better separation of the basic proteins than the process carried out in accordance with German Patent 26 29 568. A higher product yield and a higher product purity is accordingly also achieved in the process according to the invention (see Table 1).

TABLE 1

Comparison of ion exchanger chromatography of a protein mixture obtained by treatment of proinsulin (monkey proinsulin, prepared by genetic engineering by means of *E. coli*) with trypsin

| I Comparison Example in accordance with German Patent 26 29 568 | | II According to the invention |
|---|---|---|
| Exchanger: | ®TSK-DEAE anion exchanger (functional groups: diethylaminoethyl; matrix: vinyl polymer containing hydroxyl groups; manufacturer: Merck, Darmstadt) | S- ®Sepharose cation exchanger (functional groups: sulfopropyl groups; matrix: gel containing hydroxyl groups with a content of crosslinked agarose; manufacturer: Pharmacia, Sweden) |

TABLE 1-continued

Comparison of ion exchanger chromatography of a protein mixture obtained by treatment of proinsulin (monkey proinsulin, prepared by genetic engineering by means of *E. coli*) with trypsin

| I Comparison Example in accordance with German Patent 26 29 568 | | II According to the invention |
|---|---|---|
| Buffer, gradient: | tris(hydroxymethyl)amino-methane/HCl pH 9, 0.1–0.25 M NaCl | lactic acid, pH 3.5, 0.15–0.35 M NaCl |
| Dissociating agent: | 0.1% of ®Genapol SE 100 (fatty alcohol polyglycol ether, manufacturer: Hoechst AG, Frankfurt) | 30% of isopropanol |
| Loading: | 1 g/l | 3 g/l |
| Stage yield: | about 60% | about 80% |
| Purity: | 80–85% | 90–95% |
| Separation: | no complete separation between insulin-Arg-B31-32, insulin-Arg-B31 and basic impurities | Base line separation between insulin-Arg-Arg-B31-32, insulin-Arg-B31 and basic impurities |

What is claimed is:

1. A process for the isolation of basic proteins from a protein mixture containing said basic proteins obtained by enzymatic cleavage of proinsulin, or a natural, semi-synthetic, or genetically engineered derivative thereof consisting essentially of
    loading a strongly acid cation exchanger with the protein mixture; and
    eluting said proteins by means of a water and $C_1$–$C_4$ alkanol mixture of about 10 to about 50% by volume of alkanol, wherein the pH of the elution solution is about 2.5 to about 5.5.

2. The process as claimed in claim 1, wherein the strong acid cation exchanger employed contains sulfo groups.

3. The process as claimed in claim 1, wherein the loading of the strongly acid cation exchanger is carried out at a pH between about 3.5 to about 4.0.

4. The process as claimed in claim 1, wherein the mixture of water and $C_1$–$C_4$-alkanol employed for the elution contains ethanol or isopropanol as the $C_1$–$C_4$-alkanol.

5. The process as claimed in claim 1, wherein the loading elution solution also contains a buffer.

6. The process as claimed in claim 1, wherein the elution is carried out with an ammonium or alkali metal salt gradient of between about 0 to about 1 mol/l.

7. The process as claimed in claim 1, wherein the water and $C_1$–$C_4$-alkanol mixture contains about 20 to 40% by volume of alkanol.

8. The process as claimed in claim 7, wherein the water and $C_1$–$C_4$-alkanol mixture contains about 30% by volume of alkanol.

9. The process as claimed in claim 2, where the strongly acid cation exchanger employed contains sulfopropyl groups.

10. The process as claimed in claim 4, wherein the water and alkanol mixture used for the elution contains iospropanol as the alkanol.

11. The process as claimed in claim 5, wherein the buffer is an organic acid.

12. The process as claimed in claim 1, wherein the organic acid is lactic acid.

13. The process as claimed in claim 6, wherein the elution is carried out with an ammonium or alkali metal salt gradient of between about 0.15 to 0.35 mol/l.

* * * * *

UNITED STATES PATENT AND TRADEMARK OFFICE
CERTIFICATE OF CORRECTION

PATENT NO. : 5,101,013

DATED : March 31, 1992

INVENTOR(S) : Michael Doreschug and Rainer Obermeier

It is certified that error appears in the above-identified patent and that said Letters Patent is hereby corrected as shown below:

ON THE TITLE PAGE:

Item [75], "Ranier Obermeier" should be --Rainer Obermeier--.

Abstract, line 3, change "clevage" to --cleavage--.

Col. 6
Claim 10, line 3, change "iospropanol" to --isopropanol--.

Col. 6
Claim 12, line 1, change "1" to --11--.

Signed and Sealed this

Twentieth Day of July, 1993

Attest:

MICHAEL K. KIRK

*Attesting Officer*     *Acting Commissioner of Patents and Trademarks*